United States Patent [19]

Fabian et al.

[11] Patent Number: 5,329,944

[45] Date of Patent: Jul. 19, 1994

[54] SURGICAL IMPLEMENT DETECTOR UTILIZING AN ACOUSTIC MARKER

[76] Inventors: Carl E. Fabian, 577 NE. 96th St., Miami Shores, Fla. 33138; Philip M. Anderson, 37 Winding Way, Madison, N.J. 07940

[21] Appl. No.: 25,182

[22] Filed: Mar. 2, 1993

Related U.S. Application Data

[63] Continuation-in-part of Ser. No. 857,221, Mar. 25, 1992, Pat. No. 5,190,059, which is a continuation of Ser. No. 698,199, May 6, 1991, Pat. No. 5,107,862, which is a continuation of Ser. No. 437,184, Nov. 16, 1989, abandoned.

[51] Int. Cl.⁵ ............................................. A61B 19/00
[52] U.S. Cl. ..................................... 128/899; 128/654
[58] Field of Search ............... 128/899, 903, 631, 654; 604/362; 606/1

[56] References Cited

U.S. PATENT DOCUMENTS

| | | | |
|---|---|---|---|
| 4,041,954 | 8/1977 | Ohara | 128/697 |
| 4,114,601 | 9/1978 | Abels | 600/20 |
| 4,658,818 | 4/1987 | Miller, Jr. et al. | 606/1 |

*Primary Examiner*—William E. Kamm
*Assistant Examiner*—Brian M. Green
*Attorney, Agent, or Firm*—Ernest D. Buff

[57] ABSTRACT

The present invention provides a method and apparatus for accurately and reliably detecting surgical implements within animal or human tissue. The apparatus comprises a detector responsive to the presence, within a wound, of a surgical implement to which a marker is secured. The marker is adapted to produce identifying acoustic signal characteristics within the wound.

16 Claims, 7 Drawing Sheets

20

SURGICAL IMPLEMENT DETECTOR UTILIZING AN ACOUSTIC MARKER

CROSS REFERENCE TO RELATED APPLICATIONS

This application is a continuation-in-part of U.S. application Ser. No. 857,221, filed Mar. 25, 1992 now U.S. Pat. No. 5,190,059 which, in turn, is a continuation of U.S. application Ser. No. 698,199, filed May 6, 1991 now U.S. Pat. No. 5,107,862 which, in turn, is a continuation of U.S. application Ser. No. 437,184, filed Nov. 16, 1989, now abandoned.

BACKGROUND OF THE INVENTION

1. Field of the Invention

The present invention relates to a method for detecting a marked surgical implement such as a sponge, instrument, or the like inadvertently left within a surgical wound.

2. Description of the Prior Art

During the course of a surgical operation it is frequently necessary for articles, such as surgical sponges, gauzes, instruments, needles, and the like, to be placed into a wound cavity. Notwithstanding rigorous precautions attendant surgical procedures, such items are sometimes inadvertently lost during surgery and remain within the patient. When this happens, the patient can encounter serious consequences, including pain, infection, intestinal obstruction, and even death. The problem of retained surgical implements has existed since the earliest days of surgery. Procedures conventionally employed to prevent post-surgical implement retention include a manual search of the wound by the surgeon prior to closure and a careful accounting for all materials inserted and removed from the wound. The accounting function is customarily carried out by the operating room staff, usually the circulating nurse. Despite these precautionary measures the accidental retention of surgical implements continues to occur with disturbing regularity, even in prestigious institutions, and is regarded by surgeons as a major unsolved problem.

At present, manual search and physical count remain the primary methods used to prevent retained surgical implements. Most surgical instruments are composed of metal, and are easily detectable by x-ray. Sponges are usually tagged with radiopaque markers to make them also visible on x-ray, but x-rays are not routinely done at completion of the operation because of several disadvantages including inconvenience, expense, loss of operative time, and radiation exposure. Postoperative x-rays suffer from some of the same disadvantages. Moreover, even when postoperative x-rays are taken, sometimes retained items are overlooked, and even if detected, require a second operation to effect their removal.

To overcome the difficulty of detecting retained surgical implements, it has been suggested that the implements be provided with a radioactive tracer. This technique, disclosed by U.S. Pat. No. 2,740,405 to Riordan, is subject to obvious hazards associated with use, storage and disposal of radioactive materials.

It has also been proposed that surgical sponges be marked with a flexible plastic impregnated with either paramagnetic or ferromagnetic materials in the form of powders. Detection of these marked sponges is accomplished by a metal detector. This method, taught by U.S. Pat. No. 3,422,816 to Robinson et al., provides very small signals difficult to detect over the width of a patient's body. In addition, the Robinson et al. technique provides no discrimination against other metal objects, such as staples which, though present within the surgical wound, are appointed for retention therewithin.

Yet another proposal, advanced by U.S. Pat. No. 3,587,583 to Greenberg, involves use of surgical sponges marked with magnetized particles whose presence is detectable with magnetodiodes. In practice, however, the magnetic field generated by these particles is too small to be readily detected by the diodes.

U.S. Pat. No. 4,114,601 to Ables discloses the use of a small transponder fixed to a surgical sponge or instrument. This transponder exhibits gyromagnetic resonance at preselected frequencies. Detection is accomplished by nonlinear mixing of two frequencies impinging upon the transponder. The gyromagnetic resonance effect disclosed by Ables is a high frequency phenomenon, existing at frequencies of the order of about 5 gigahertz (5,000,000,000 cycles/sec). These frequencies, known as microwaves, are absorbed readily by animal tissue and are, in fact, used in microwave ovens for cooking. In use of the Ables type transponder, the energy developed goes primarily into heating tissue, rather than exciting the transponder into gyromagnetic resonance.

U.S. Pat. No. 5,057,095 to Fabian discloses the use of a resonant transponder fixed to a surgical sponge or instrument, and U.S. Pat. No. 5,105,829 to Fabian and Anderson discloses a surgical implement detector utilizing capacitive coupling.

SUMMARY OF THE INVENTION

The present invention provides a method and apparatus for accurately and reliably detecting surgical implements within animal or human tissue. The apparatus comprises a detector responsive to the presence, within a wound, of a surgical implement to which a marker is secured. The marker is adapted to produce identifying signal characteristics within the wound and to be detected with a transducer in contact with the tissue.

Generally stated the apparatus for detecting a surgical implement within a wound in human or animal tissue, comprises: a marker secured to a surgical implement positioned within the wound, the marker being battery powered; an acoustic signal generating means for generating an acoustic signal; a signal generating means for generating a signal having a predetermined frequency band and being operative to cause the acoustic signal generating means to generate the acoustic signal, providing the marker with signal identity; and a detection means having a transducer in contact with the tissue.

More specifically, the marker comprises a miniature acoustic transmitter enclosed within a water-tight case. The case is comprised of a plastic that remains inert to the body for the duration of the surgery. The transmitter is comprised of a battery, an electronic circuit, and an acoustic transducer, and is adapted to provide a unique identifying acoustic signal. A detector placed in contact with the tissue is adapted, irrespective of the orientation of such marker, to detect the marker signal and record such detection with visual and/or audio indicators. Alternatively, the detector is a stethoscope.

In order to conserve battery energy, various means are described herein whereby generation of the acoustic signal is initiated by operating room personnel proximate to the time of the surgical operation. This is achieved by various starting means, either prior to placement of the marker within the surgical wound or, alternately, by signal starting means activated external to the body. Examples of each of these alternate types of starting means are described hereinafter in greater detail.

Advantageously, the method and apparatus of the invention detect retention of surgical implements with far greater accuracy than methods and means involving a physical count of implements that enter and exit the wound. The apparatus is inexpensive to construct, safer for the patient than postoperative X-rays and avoids risk to the environment posed by radioactive tracers. Generation of a strong acoustic signal is effected in a highly reliable manner. The acoustic signal is more easily detected, such as by the unassisted ear or by a stethoscope, than electromagnetic signals generated by electromagnetic detection systems, and is generated without the heating of tissue caused by RF detection systems. The present invention has a further advantage over electromagnetic systems in that there is no possibility of interference with patient monitoring systems, such as EKG systems and the like.

BRIEF DESCRIPTION OF THE DRAWINGS

The invention will be more fully understood and further advantages will become apparent when reference is made to the following detailed description of the preferred embodiment of the invention and the accompanying drawings in which.

DESCRIPTION OF THE PREFERRED EMBODIMENTS

Figure 1:
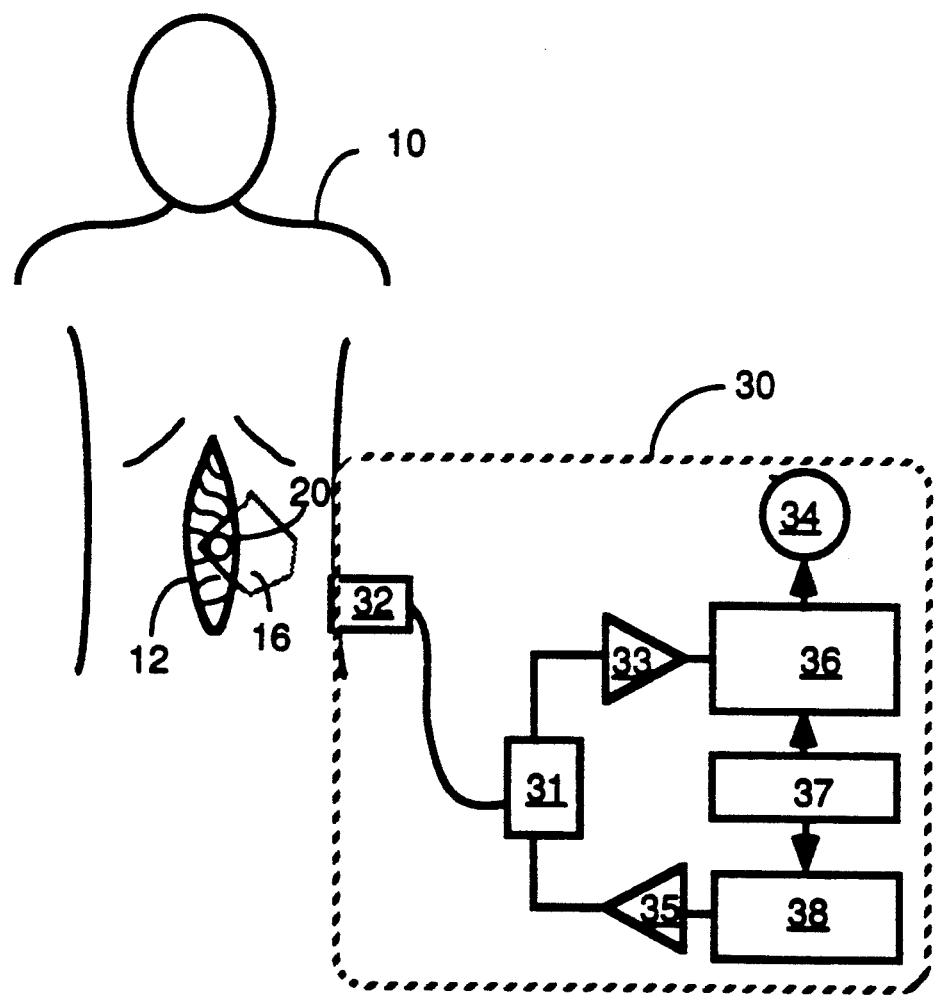
FIG. 1 is a block diagram of a surgical implement detector incorporating the present invention.
Figure 2:
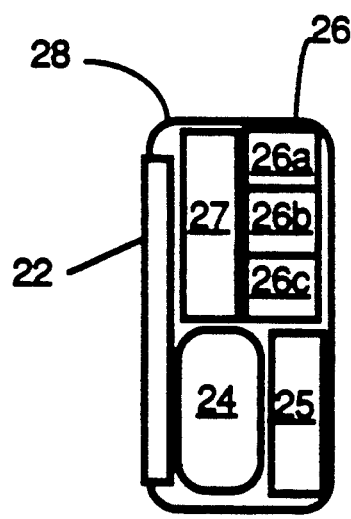
FIG. 2 is a block diagram of a marker suited for use in the detector of FIG. 1.
Figure 3:
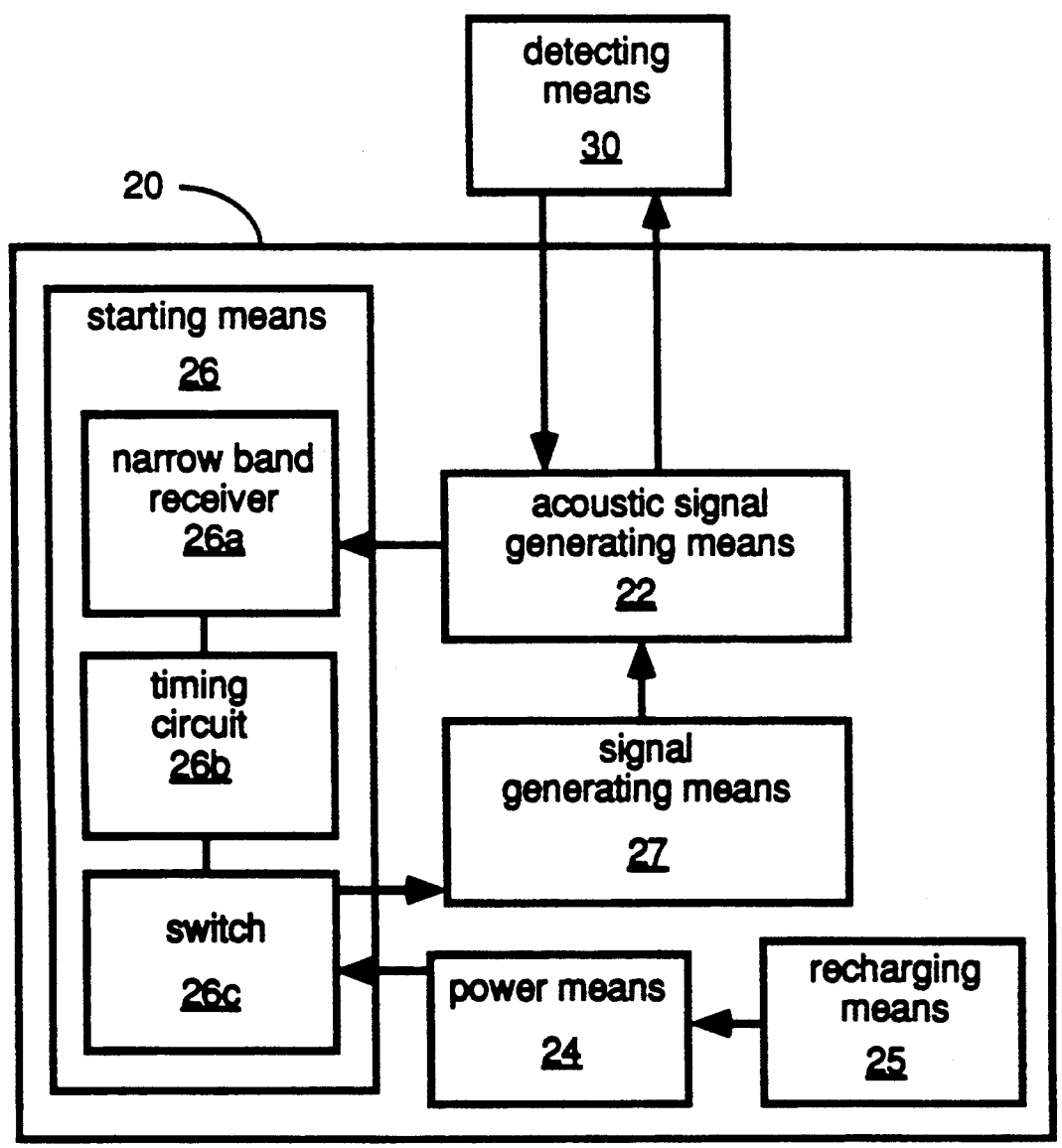
FIG. 3 is a block diagram of the signal path of a surgical implement detector incorporating the present invention.

Referring to the drawings, there is shown in FIG. 1 a block diagram of a surgical implement detector incorporating the present invention. A marker 20 is secured to a surgical implement 16, such as a sponge, positioned within the wound. The marker 20 has means for generating an acoustic signal within a surgical wound 12 in patient 10. The marker, shown generally at 20 in FIG. 2, consists of a case 28 comprised of a material, such as ABS plastic, that will remain inert within the wound for the period of the surgery. Within the case 28 is housed a signal generating means 27, a starting means 26, a power means 24, and a recharging means 25. Acoustic signal generating means 22 is positioned so as to protrude through one side of case 28. Alternatively, acoustic signal generating means 22 is positioned within the case 28. Preferably, acoustic signal generating means 22 is a piezoelectric element. Upon being activated, the starting means 26 causes the power means 24 to be connected to the signal generating means 27 which, in turn, is connected to the acoustic signal generating means 22. The resulting acoustic signal is transmitted within wound 12 for a predetermined period of time. Preferably, the acoustic signal is periodic. The starting means 26 is comprised of a narrow band receiver 26a electrically connected to acoustic signal generating means 22, a timing circuit 26b, and a switch 26c. Narrow band receiver 26a is tuned to receive via acoustic transducer 22 an initialization signal from detector 30. Timing circuits are well known in the art and can be constructed from a type 555 timer, where a resistor and capacitor set said predetermined time. Switch 26c is typically a simple transistor. The activation signal is provided by detector 30. The relationship between the elements of the surgical implement detector is shown in schematic form in FIG. 3.

The power means 24 is typically a rechargeable battery, such as NiCd, periodically refreshed by the recharging means 25. The recharging means 25 is comprised of a coil of wire connected to an ac to dc rectifier. An external ac source is inductively coupled via a coil to the coil in the recharging means 25. Alternatively, the recharging means 25 is comprised of two external contacts through the case 28. Recharging is accomplished by direct connection with an external dc source.

The detector 30, as shown in FIG. 1, comprises an acoustic transducer 32, a signal processor 36 and its filtering preamplifier 33, a controller 37, electronic switch 31, initialization generator 38 and its amplifier 35, and an indicator 34. When activated by operating room personnel, the controller 37 causes the electronic switch 31 to connect acoustic transducer 32 to amplifier 35. The controller 37 next causes the initialization generator 38 to generate a single signal burst or, alternatively, a periodic signal burst, enhanced by amplifier 35 and transmitted through electronic switch 31 and acoustic transducer 32 to the marker 20, thereby activating the marker's starting means 26 as described above. The signal transmitted into the surrounding tissue by the marker 20 is received by the detector 30 through its acoustic transducer 32, placed in contact with patient 10 near wound 12. The controller next causes electronic switch 31 to connect acoustic transducer 32 to filtering preamplifier 33. After filtering and amplification by preamp 33 and verification of the received signal by the processor 36, the indicator 34 is activated. The indicator is comprised of visual and/or aural transducers, such as a light and/or a buzzer.

Figure 4:
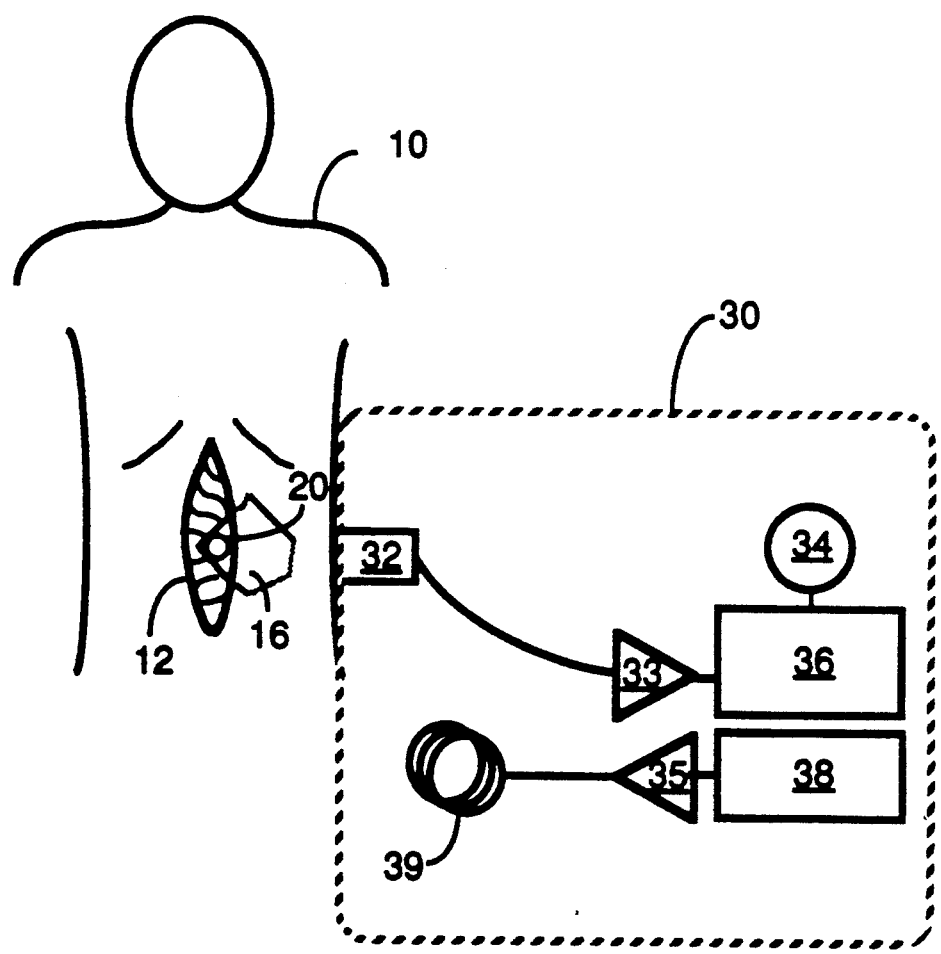
FIG. 4 is a block diagram of a surgical implement detector incorporating an electromagnetic initialization signal.

Alternatively, as shown in FIG. 4, electronic switch 31 is eliminated and amplifier 35 directly powers an antenna 39 to generate an electromagnetic initialization signal. The tuned receiver 26a of starting means 26 is connected to a receiving coil.

As a further alternative, the power means 24 is not rechargeable but comprises an alkaline or lithium battery. Preferably, the acoustic signal transmitted by marker 20 is periodic. In this manner, power usage is minimized and battery life is maximized- The marker construction is simplified by elimination of the recharging means 25.

Figure 5:
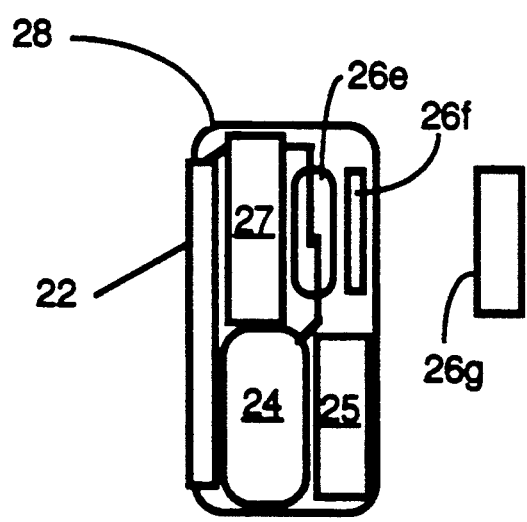
FIG. 5 is a diagram of a marker with a reed-switch starting means.
Figure 6:
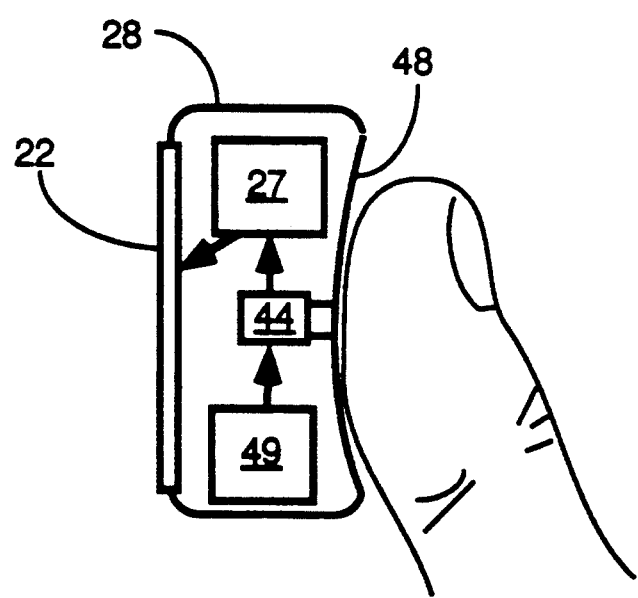
FIG. 6 is a side-view diagram of a pressure sensitive switch starting means.

FIG. 5 shows marker 20 in a second embodiment of the invention. Electronic switch 31, initialization generator 38, and amplifier 35 of detector 30 are eliminated. With this embodiment, the starting means 26 of marker 20 must be manually activated by operating room personnel before the marked implement 16 is placed within the wound 12. Marker 20 is rechargeable or, alternatively, non-rechargeable as described in the previous embodiment. The starting means 26 is comprised of a normally-open magnetic reed switch 26e and switching magnet 26f. Switching magnet 26f is magnetized by temporarily bringing magnet 26g in close proximity to switching magnet 26f in such a manner that the field of magnet 26g is parallel with the length of switching magnet 26f. Magnetic reed switch 26e closes due to field of magnetized switching magnet 26f, thereby connecting power means 24 to signal generating means 27. Conversely, temporarily bringing magnet 26g in close proximity to switching magnet 26f in such a manner that the field of magnet 26g is perpendicular with the length of switching magnet 26f causes magnetic reed switch 26e to open, therefore disconnecting power means 24. The detector 30 receives and processes acoustic signals as in the previous embodiment. Alternatively, the detector comprises a simple stethoscope. As a further alternative, the unassisted ear is used to detect the identifying acoustic signal. Alternatively, as shown in FIG. 6, starting means 26 is comprised of an activation switch 44 mounted within case 28. Case 28 has at least one flexible side 48 provided for engaging activation switch 44. Before insertion in the wound, marker 20 is activated by manually pressing against flexible side 48, causing activation switch 44 to close, and thereby connecting battery 49 to signal generating means 27, there in turn causing acoustic signal generating means 22 to generate an acoustic signal within wound 12. The detector 30 receives and processes acoustic signals as in the previous embodiment. Alternatively, the detector comprises a simple stethoscope. As a further alternative, the unassisted ear is used to detect the identifying acoustic signal. Repressing flexible side 48 causes activation switch 44 to open, disconnecting battery 49 from signal generating means 27, thereby terminating the identifying acoustic signal.

Figure 7:
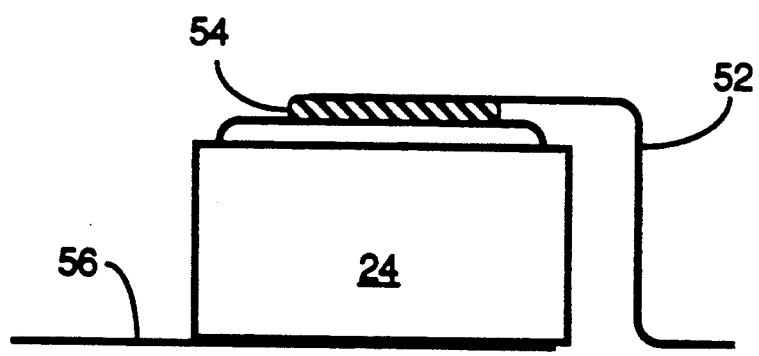
FIG. 7 is a side-view diagram of a wax-spacer switch starting means.

In a third embodiment of the invention, described with reference to FIG. 7, the starting means can be activated only once, the activation being accomplished by operating room staff prior to the marker's first use. The marker's power means 24 is non-rechargeable and the recharging means 25 is eliminated. The starting means 26 is heat-activated and it is comprised of a spring-loaded battery contact 52 and an insulating wax spacer 54. Alternatively, battery 24 is coated with wax 54, thereby electrically insulating battery contacts 52 and 56 from battery 24. The wax 54 is selected to have a melting point, preferably at the standard operating point of gas sterilizers, approximately 140 degrees Fahrenheit. Beeswax and paraffin meet this criterion. Melting of the wax 54 causes the spring-loaded or cantilevered contacts 52 and 56 to close against battery 24 energizing the signal generating means 27, whereby marker 20 transmits a periodic signal. Detector 30 works as described in the previous embodiment.

To further illustrate the present invention, a marker was provided with a small piezoelectric disk, emitting a pulsating audible signal powered by a battery connected to an activation switch and tested within a human cadaver. A midline abdominal incision was created, and an activated marker was inserted into the peritoneal cavity, variously placed in multiple positions including both flanks, between the leaves of the mesentary, under the liver, and in various recesses. In each instance, the acoustic signal produced by the marker was readily detected with a stethoscope positioned on the body wall, including against the subject's back. Additionally, the acoustic signal produced by the marker was also readily detected with the unassisted ear.

Having thus described the invention in rather full detail, it will be understood that such detail need not be strictly adhered to but that further changes may suggest themselves to one having ordinary skill in the art, all falling within the scope of the invention as defined by the subjoined claims.

What is claimed is:

1. An apparatus for detecting a surgical implement within a wound in human or animal tissue, comprising:
   (a) a marker secured to a surgical implement adapted to be positioned within said wound, said marker having a battery and being powered thereby;
   (b) acoustic signal generating means for generating an acoustic signal;
   (c) signal generating means for generating a signal having a predetermined frequency band and being operative to cause said acoustic generating means to generate said acoustic signal, providing said marker with signal identity, said signal generating means receiving power from said battery; and
   (d) detection means having a transducer in contact with human or animal tissue, for detecting said acoustic signal.

2. An apparatus as recited in claim 1, wherein said marker further comprises a starting means.

3. An apparatus as recited in claim 2, wherein said starting means is adapted to connect said battery to said signal generating means to cause said marker to be activated.

4. An apparatus as recited in claim 1, wherein said detection means further includes an indicating means for providing an audible or visible alarm when said marker is activated.

5. An apparatus as recited in claim 1, wherein said detection means comprises means for causing said starting means to activate said marker.

6. An apparatus as recited in claim 5, wherein said means for causing said starting means to activate is a second acoustic signal from said detection means.

7. An apparatus as recited in claim 5, wherein said means for causing said starting means to activate is an electromagnetic signal from said detection means.

8. An apparatus as recited in claim 1, wherein said marker further comprises a recharging means.

9. An apparatus as recited in claim 8, wherein said recharging means of said marker is adapted to be inductively coupled to an external ac power source.

10. An apparatus as recited in claim 9, wherein said recharging means of said marker is adapted to be directly coupled to an external dc power source.

11. An apparatus as recited in claim 2, wherein said starting means of said marker comprises a magnetically activated reed switch and a switching magnet.

12. An apparatus as recited in claim 2, wherein said starting means of said marker comprises a mechanical switch provided with a means to be closed when a side of said marker is pressed.

13. An apparatus as recited in claim 3, wherein said starting means of said marker comprises two spring loaded contacts separated by wax.

14. A marker attached to a surgical implement within a wound in human or animal tissue, comprising:
   (a) a battery;

(b) acoustic signal generating means for generating an acoustic signal;
(c) signal generating means for generating a signal having a predetermined frequency band and being operative to cause said acoustic generating means to generate said acoustic signal, providing said marker with signal identity, said signal generating means receiving power from said battery.

15. A method for detecting a surgical implement within a wound in human or animal tissue, comprising the steps of:
(a) attaching a marker to said surgical implement prior to its disposition within said wound, the marker having a battery and being powered thereby;
(b) generating a signal from a signal generating means having a predetermined frequency band and being operative to initiate generation of an acoustic signal, from an acoustic signal generating means providing said marker with signal identity;
(c) receiving said acoustic signal by a transducer in contact with said tissue near said wound to detect said marker; and
(d) indicating said detection with detection means.

16. A method for detecting a surgical implement within a wound in human or animal tissue, comprising the steps of:
(a) attaching a marker to a surgical implement prior to its disposition within said wound, the marker being battery powered;
(b) generating a first acoustic signal with a detection means, said acoustic signal having a first acoustic predetermined frequency band;
(c) detecting said first acoustic signal with detection means thereby activating said marker;
(d) generating signal from a signal generating means having a signal predetermined frequency band and being operative to initiate generation of a second acoustic signal from an acoustic signal generating means providing said marker with signal identity;
(e) receiving said second acoustic signal by a transducer in contact with said tissue near said wound to detect said marker; and
(f) indicating said detection of the marker with detection means.

* * * * *